United States Patent
Lechtman

(10) Patent No.: US 6,551,262 B1
(45) Date of Patent: Apr. 22, 2003

(54) HANDHELD FOOT MANICURING DEVICE

(76) Inventor: Nirit Lechtman, 430 1/2 S. Doheny Dr., Beverly Hills, CA (US) 90211

( * ) Notice: Subject to any disclaimer, the term of this patent is extended or adjusted under 35 U.S.C. 154(b) by 0 days.

(21) Appl. No.: 09/849,420

(22) Filed: May 4, 2001

(51) Int. Cl.[7] ................................................ A61H 7/00
(52) U.S. Cl. ........................ 601/144; 601/143; 451/355
(58) Field of Search .............................. 601/84, 85, 87, 601/118, 120, 121, 122, 124–127, 130, 132, 136–138, 143, 144, 23, 28–29, 32, 112; 132/76.4; 451/355, 303, 296; 606/131, 133

(56) References Cited

U.S. PATENT DOCUMENTS

| | | | |
|---|---|---|---|
| 2,597,525 A | 5/1952 | Kessler | |
| 2,714,788 A | * 8/1955 | Giovanna | 132/73.6 |
| 2,718,735 A | * 9/1955 | Hamilton | 451/355 |
| 3,131,701 A | 5/1964 | Emerson | |
| 3,675,324 A | * 7/1972 | Yamada et al. | 30/43.6 |
| 3,733,634 A | 5/1973 | Golbe | |
| 3,884,224 A | * 5/1975 | Garcia | 601/144 |
| 4,083,327 A | * 4/1978 | Dowdy | 119/601 |
| 4,360,906 A | * 11/1982 | Shitama | 15/23 |
| 4,615,461 A | * 10/1986 | Liu | 206/45.23 |
| 4,643,207 A | * 2/1987 | Grahame | 132/73.6 |
| 4,694,616 A | * 9/1987 | Lindberg | 451/355 |
| D301,738 S | 6/1989 | Daar et al. | |
| 4,858,390 A | * 8/1989 | Kenig | 451/296 |
| 4,985,999 A | * 1/1991 | Iwasaki et al. | 30/133 |
| 5,082,009 A | * 1/1992 | Cromer | 132/73 |
| 5,385,532 A | 1/1995 | Shyu | |
| 5,643,062 A | * 7/1997 | Joseph et al. | 451/296 |
| 5,704,902 A | * 1/1998 | Vandenbelt et al. | 601/46 |
| 5,864,746 A | * 1/1999 | Chang | 451/296 |
| 5,868,688 A | 2/1999 | Avidor et al. | |
| 6,001,070 A | * 12/1999 | Gebhard | 601/15 |
| 6,363,947 B1 | * 4/2002 | Wu | 132/294 |

* cited by examiner

Primary Examiner—Justine R. Yu

(57) ABSTRACT

A handheld foot manicuring device for scrubbing and manicuring a user's feet. The handheld foot manicuring device includes a housing assembly including a housing member having a head portion and a handle portion and further having a front wall and a back wall; and also includes a drive assembly including roller members being rotatably mounted to the housing member; and further includes an endless pad member being removably carried about the roller members and having a textured outside and being adapted to exfoliate a user's foot.

12 Claims, 2 Drawing Sheets

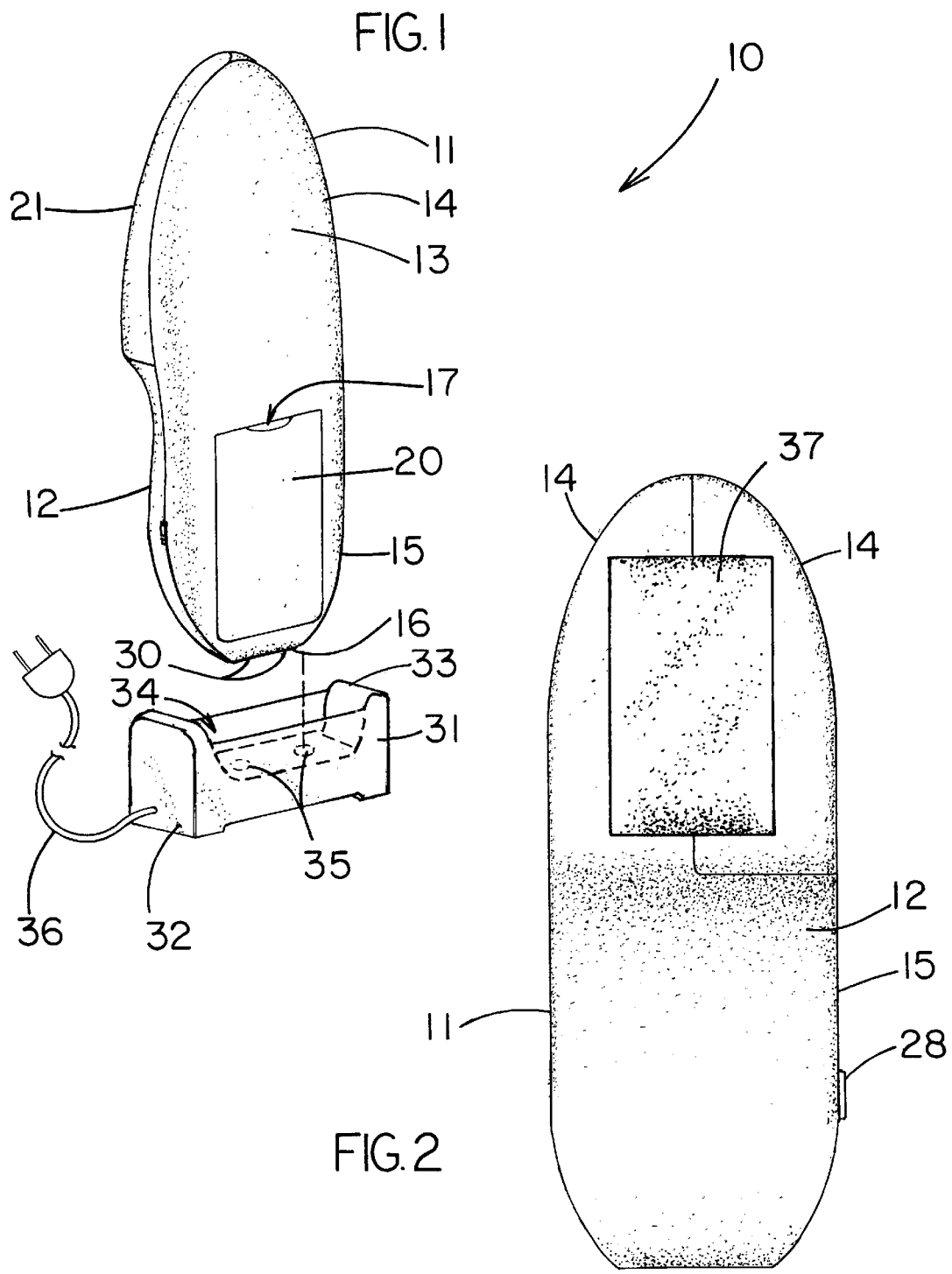

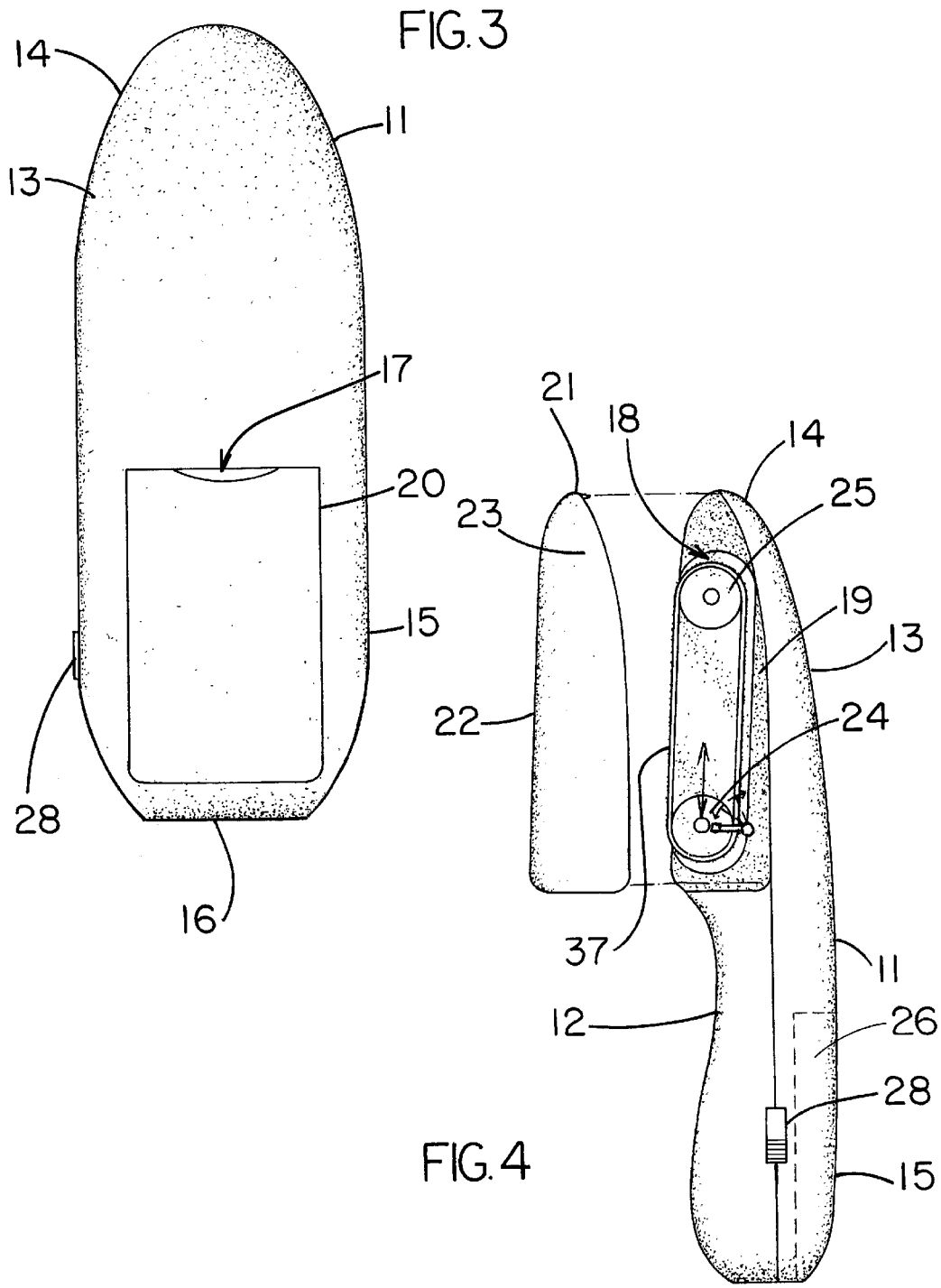

HANDHELD FOOT MANICURING DEVICE

BACKGROUND OF THE INVENTION

1. Field of the Invention

The present invention relates to a handheld foot scrubber and more particularly pertains to a new handheld foot manicuring device for scrubbing and manicuring a user's feet.

2. Description of the Prior Art

The use of a handheld foot scrubber is known in the prior art. More specifically, a handheld foot scrubber heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 3,733,634; 2,597,525; 3,131,701; U.S. Pat. No. Des. 301,738; U.S. Pat. Nos. 5,385,532; and 5,858,688.

While these devices fulfill their respective, particular objectives and requirements, the aforementioned patents do not disclose a new handheld foot manicuring device. The inventive device includes a housing assembly including a housing member having a head portion and a handle portion and further having a front wall and a back wall; and also includes a drive assembly including roller members being rotatably mounted to the housing member; and further includes an endless pad member being removably carried about the roller members and having a textured outside and being adapted to exfoliate a user's foot.

In these respects, the handheld foot manicuring device according to the present invention substantially departs from the conventional concepts and designs of the prior art, and in so doing provides an apparatus primarily developed for the purpose of scrubbing and manicuring a user's feet.

SUMMARY OF THE INVENTION

In view of the foregoing disadvantages inherent in the known types of handheld foot scrubber now present in the prior art, the present invention provides a new handheld foot manicuring device construction wherein the same can be utilized for scrubbing and manicuring a user's feet.

The general purpose of the present invention, which will be described subsequently in greater detail, is to provide a new handheld foot manicuring device which has many of the advantages of the handheld foot scrubber mentioned heretofore and many novel features that result in a new handheld foot manicuring device which is not anticipated, rendered obvious, suggested, or even implied by any of the prior art handheld foot scrubber, either alone or in any combination thereof.

To attain this, the present invention generally comprises a housing assembly including a housing member having a head portion and a handle portion and further having a front wall and a back wall; and also includes a drive assembly including roller members being rotatably mounted to the housing member; and further includes an endless pad member being removably carried about the roller members and having a textured outside and being adapted to exfoliate a user's foot.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new handheld foot manicuring device which has many of the advantages of the handheld foot scrubber mentioned heretofore and many novel features that result in a new handheld foot manicuring device which is not anticipated, rendered obvious, suggested, or even implied by any of the prior art handheld foot scrubber, either alone or in any combination thereof.

It is another object of the present invention to provide a new handheld foot manicuring device which may be easily and efficiently manufactured and marketed.

It is a further object of the present invention to provide a new handheld foot manicuring device which is of a durable and reliable construction.

An even further object of the present invention is to provide a new handheld foot manicuring device which is susceptible of a low cost of manufacture with regard to both materials and labor, and which accordingly is then susceptible of low prices of sale to the consuming public, thereby making such handheld foot manicuring device economically available to the buying public.

Still yet another object of the present invention is to provide a new handheld foot manicuring device which provides in the apparatuses and methods of the prior art some of the advantages thereof, while simultaneously overcoming some of the disadvantages normally associated therewith.

Still another object of the present invention is to provide a new handheld foot manicuring device for scrubbing and manicuring a user's feet.

Yet another object of the present invention is to provide a new handheld foot manicuring device which includes a housing assembly including a housing member having a head portion and a handle portion and further having a front wall and a back wall; and also includes a drive assembly including roller members being rotatably mounted to the housing member; and further includes an endless pad member being removably carried about the roller members and having a textured outside and being adapted to exfoliate a user's foot.

Still yet another object of the present invention is to provide a new handheld foot manicuring device that is easy and convenient to use.

Even still another object of the present invention is to provide a new handheld foot manicuring device that safely rejuvenates one's feet by exfoliating dry skin, removing calluses and softening painful corns.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new handheld foot manicuring device according to the present invention.

FIG. 2 is a front elevational view of the present invention.

FIG. 3 is a back elevational view of the present invention.

FIG. 4 is a side elevational view of the present invention.

DESCRIPTION OF THE PREFERRED EMBODIMENT

With reference now to the drawings, and in particular to FIGS. 1 through 4 thereof, a new handheld foot manicuring device embodying the principles and concepts of the present invention and generally designated by the reference numeral 10 will be described.

As best illustrated in FIGS. 1 through 4, the handheld foot manicuring device 10 generally comprises a housing assembly including a housing member 11 having a head portion 14 and a handle portion 15 and further having a front wall 12 and a back wall 13. The housing member 11 further includes an opening 17 being disposed through the back wall 13 and in the handle portion 15, and also includes a slot 18 being disposed in the front wall 12 and in the head portion 14. The front wall 12 along the handle portion 14 is contoured to facilitate gripping thereof by a user. The head portion 14 is tapered toward a top end of the housing member 11. The housing member 11 also includes recessed portions 19 disposed in sides of the head portion 14. The housing assembly further includes a first cover 20 being removably disposed over the opening 17, and also includes a second cover 21 being removably disposed over the slot 18. The second cover 21 has a main wall 22 and side walls 23 which are movably received upon the recessed portions 19 of the head portion 14. The housing member 11 has a length of approximately 7½ inches, a width of approximately 2 inches, and a thickness of approximately 1½ inches.

A drive assembly includes roller members 24,25 being rotatably and conventionally mounted to the housing member 11. The roller members 24,25 are laterally spaced apart in the slot 19 of the head portion 14 with a first of the roller members 24 being movable relative to a second of the roller members 25. The drive assembly further includes a battery pack 26 being removably disposed in the handle portion 15 of the housing member 11, and also includes a motor 27 being conventionally disposed in the housing member 11 and being conventionally connected to the battery pack 26 and to the roller members 24,25, and further includes a switch member 28 being movably and conventionally mounted upon the housing member 11 and being conventionally connected to the battery pack 26 and to the motor 27 for energizing the motor 27, and also includes a remote battery charger 31 having a housing 32 and a power cord 36 being conventionally attached to the housing 32, and further includes battery contact members 30 being conventionally disposed in a bottom end 16 of the housing member 11, and also including a lever 29 being conventionally disposed in the housing member 11. The housing 32 includes a top wall 33 having a recessed portion 34 disposed therein and being adapted to receive and support the bottom end 16 of the housing member 11. The top wall 33 of the housing 32 further has charger contact members 35 being conventionally disposed in the recessed portion 34 of the housing 32 and being in contactable relationship with the battery contact members 30 for charging the battery pack 26.

An endless pad member 37 is removably carried about the roller members 24,25 and has a textured outside and is adapted to exfoliate a user's foot. The endless pad member 37 is generally sandpaper of varying coarseness. The lever 29 is engagable to the first roller member 24 for moving the first roller member 24 to facilitate loading and unloading of the endless pad member 37 about the roller members 24,25.

In use, the user places the endless pad member 37 upon the bottom of one's foot and turns on the roller members 24,25 which moves the endless pad member 37 about the roller members 24,25 and upon the bottom of one's foot to scrub and exfoliate the dry skin, the calluses, and the corns found on one's foot.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A handheld foot manicuring device comprising:
   a housing assembly including a housing member having a head portion and a handle portion and further having a front wall and a back wall;
   a drive assembly including roller members being rotatably mounted to said housing member;

an endless pad member being removably carried about said roller members and having a textured outer side and being adapted to exfoliate a user's foot, said housing member having a top end, a bottom end, and a pair of sides;

wherein said housing member further includes an opening disposed through said back wall and in said handle portion, and also includes a slot disposed in said front wall and in said head portion;

wherein said head portion also includes recessed portions disposed in each of said sides of said housing member;

wherein said housing assembly further includes a first cover being removably disposed over said opening, and also includes a second cover being removably disposed over said slot, said second cover having a main wall and side walls which are movably received upon said recessed portions of said head portion;

wherein said roller members are laterally spaced apart in said slot of said head portion and being oriented substantially parallel to each other, a first of said roller members being movable relative to a second of said roller members for facilitating the placement of said endless pad member about each of said roller members; and a longitudinal axis of each of said roller members being positioned substantially perpendicular to a longitudinal axis of said housing assembly, said roller members positioning said endless pad member along the longitudinal axis of said housing assembly such that said housing assembly is adapted for providing easier positioning of said endless pad member when said endless pad member is being used on a foot of the user.

2. A handheld foot manicuring device as described in claim 1, wherein a portion of said front wall located along said handle portion is contoured to facilitate gripping by a hand of a user, said head portion being tapered toward said top end of said housing member.

3. A handheld foot manicuring device as described in claim 1, wherein said roller members are laterally spaced apart in said slot of said head portion and being oriented substantially parallel to each other, a first of said roller members being movable relative to a second of said roller members.

4. A handheld foot manicuring device as described in claim 1, wherein said drive assembly further includes a battery pack being removably disposed in said handle portion of said housing member, and further includes a switch member being movably mounted upon said housing member and being connected to said battery pack, and also includes a remote battery charger having a housing and a power cord being attached to said housing, and further includes battery contact members being disposed in said bottom end of said housing member.

5. A handheld foot manicuring device as described in claim 4, wherein said housing of said battery charger includes a top wall having a recessed portion disposed therein and being adapted to receive and support said bottom end of said housing member, said top wall of said housing further having charger contact members being disposed in said recessed portion of said housing and being in contactable relationship with said battery contact members for charging said battery pack.

6. A handheld foot manicuring device as described in claim 1, wherein said endless pad member comprises an abrasive material of varying coarseness, a lever being engagable to said first roller member for moving said first roller member to facilitate loading and unloading of said endless pad member about said roller members.

7. A handheld foot manicuring device comprising:

a housing assembly including a housing member having a head portion and a handle portion and further having a front wail and a back wall;

a drive assembly including roller members being rotatably mounted to said housing member;

an endless pad member being removably carried about said roller members and having a textured outerside and being adapted to exfoliate a user's foot, said housing member having a top end, a bottom end, and a pair of sides;

wherein said housing member further includes an opening disposed through said back wall and in said handle portion, and also includes a slot disposed in said front wall and in said head portion;

wherein said front wall along said handle portion is contoured to facilitate gripping thereof by a user, said head portion being tapered toward a top end of said housing member;

wherein said head portion also includes recessed portions disposed in each of said sides of said housing member;

wherein said housing assembly further includes a first cover being removably disposed over said opening, and also includes a second cover being removably disposed over said slot, said second cover having a main wall and side walls which are movably received upon said recessed portions of said head portion; and a longitudinal axis of each of said roller members being positioned substantially perpendicular to a longitudinal axis of said housing assembly, said roller members positioning said endless pad member along the longitudinal axis of said housing assembly such that said housing assembly is adapted for providing easier positioning of said endless pad member when said endless pad member is being used on a foot of the user.

8. A handheld foot manicuring device as described in claim 7, wherein said drive assembly further includes a battery pack being removably disposed in said handle portion of said housing member, and further includes a switch member being movably mounted upon said housing member and being connected to said battery pack and also includes a remote battery charger having a housing and a power cord being attached to said housing, and further includes battery contact members being disposed in said bottom end of said housing member.

9. A handheld foot manicuring device as described in claim 8, wherein said housing of said battery charger includes a top wall having a recessed portion disposed therein and being adapted to receive and support said bottom end of said housing member, said top wall of said housing further having charger contact members being disposed in said recessed portion of said housing and being in contactable relationship with said battery contact members for charging said battery pack.

10. A handheld foot manicuring device as described in claim 7, wherein said endless pad member comprises an abrasive material of varying coarseness, a lever being engagable to said first roller member for moving said first roller member to facilitate loading and unloading of said endless pad member about said roller members.

11. A handheld foot manicuring device as described in claim 5, wherein said roller members are laterally spaced apart in said slot of said head portion and being oriented substantially parallel to each other, a first of said roller members being movable relative to a second of said roller members.

12. A handheld foot manicuring device comprising:

a housing assembly including a housing member having a head portion and a handle portion and further having a front wall and a back wall, said housing member further including an opening disposed through said back wall and in said handle portion, and also including a slot disposed in said front wall and in said head portion, said front wall along said handle portion being contoured to facilitate gripping thereof by a user, said head portion being tapered toward a top end of said housing member, said housing member also including recessed portions disposed in sides of said head portion, said housing assembly further including a first cover being removably disposed over said opening, and also including a second cover being removably disposed over said slot, said second cover having a main wall and side walls which are movably received upon said recessed portions of said head portion, said housing member having a length of approximately 7½ inches, a width of approximately 2 inches, and a thickness of approximately 1½ inches;

a drive assembly including roller members being rotatably mounted to said housing member, said roller members being laterally spaced apart in said slot of said head portion with a first of said roller members being movable relative to a second of said roller members, said drive assembly further including a battery pack being removably disposed in said handle portion of said housing member, and further including a switch member being movably mounted upon said housing member and being connected to said battery pack, and also including a remote battery charger having a housing and a power cord being attached to said housing, and further including battery contact members being disposed in a bottom end of said housing member, and also including a lever being disposed in said housing member, said housing including a top wall having a recessed portion disposed therein and being adapted to receive and support said bottom end of said housing member, said top wall of said housing further having charger contact members being disposed in said recessed portion of said housing and being in contactable relationship with said battery contact members for charging said battery pack;

an endless pad member being removably carried about said roller members and having a textured outerside and being adapted to exfoliate a user's foot, said endless pad member comprises an abrasive material of varying coarseness, said lever being engagable to said first roller member for moving said first roller member to facilitate loading and unloading of said endless pad member about said roller members; and a longitudinal axis of each of said roller members being positioned substantially perpendicular to a longitudinal axis of said housing assembly, said roller members positioning said endless pad member along the longitudinal axis of said housing assembly such that said housing assembly is adapted for providing easier positioning of said endless pad member when said endless pad member is being used on a foot of the user.

* * * * *